(12) United States Patent
Matsuura et al.

(10) Patent No.: US 7,978,816 B2
(45) Date of Patent: Jul. 12, 2011

(54) RADIOGRAPHIC IMAGING CONTROL APPARATUS USING MULTI RADIATION GENERATING APPARATUS

(75) Inventors: Tomohiko Matsuura, Tokyo (JP); Masahiko Okunuki, Akiruno (JP); Osamu Tsujii, Kawasaki (JP); Kazuhiro Matsumoto, Saitama (JP); Hiroyuki Shinbata, Tama (JP); Yuichi Nishii, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 26 days.

(21) Appl. No.: 12/514,076

(22) PCT Filed: Nov. 7, 2007

(86) PCT No.: PCT/JP2007/072045
§ 371 (c)(1),
(2), (4) Date: May 7, 2009

(87) PCT Pub. No.: WO2008/056814
PCT Pub. Date: May 15, 2008

(65) Prior Publication Data
US 2010/0008465 A1   Jan. 14, 2010

(30) Foreign Application Priority Data
Nov. 9, 2006 (JP) .................................. 2006-303538

(51) Int. Cl.
*G01N 23/04* (2006.01)
(52) U.S. Cl. ...................................... 378/62; 378/98.12
(58) Field of Classification Search ................ 378/9, 62, 378/98.12
See application file for complete search history.

(56) References Cited

U.S. PATENT DOCUMENTS

| | | | |
|---|---|---|---|
| 6,018,562 A | 1/2000 | Willson | |
| 6,088,425 A | 7/2000 | Ono | |
| 6,674,837 B1 | 1/2004 | Taskar et al. | |
| 7,103,139 B2 | 9/2006 | Nagaoka et al. | |
| 7,333,587 B2 | 2/2008 | De Man | |
| 7,639,775 B2 | 12/2009 | De Man | |
| 2005/0100126 A1 | 5/2005 | Mistretta et al. | |
| 2005/0100127 A1 | 5/2005 | Zhao et al. | |
| 2005/0190878 A1* | 9/2005 | De Man et al. | 378/9 |
| 2005/0226364 A1 | 10/2005 | Bernard De Man et al. | |
| 2009/0161816 A1 | 6/2009 | De Man | |

FOREIGN PATENT DOCUMENTS

| | | |
|---|---|---|
| CN | 1672637 A | 9/2005 |
| EP | 1005257 A | 5/2008 |
| JP | 04-288147 A | 10/1992 |

(Continued)

OTHER PUBLICATIONS

J. Zhang, et al, Stationary scanning x-ray source based on carbon nanotube field emitters, Applied Physics Letters 86, 184104 (2005).

*Primary Examiner* — Hoon Song
(74) *Attorney, Agent, or Firm* — Canon U.S.A., Inc. I.P. Division

(57) ABSTRACT

A control apparatus for controlling a multi radiation generating apparatus having a plurality of radiation generating devices which irradiate a two-dimensional sensor with radiation sets the intensity of radiation with which the plurality of radiation generating devices irradiate the two-dimensional sensor based on information about a part or physique of a patient, which is input by an input device.

18 Claims, 16 Drawing Sheets

FOREIGN PATENT DOCUMENTS

| | | |
|---|---|---|
| JP | 06-038957 A | 2/1994 |
| JP | 06-078914 A | 3/1994 |
| JP | 06-038915 U | 5/1994 |
| JP | 06-233757 A | 8/1994 |
| JP | 07-031609 A | 2/1995 |
| JP | 08-280659 A | 10/1996 |
| JP | 10-071141 A | 3/1998 |
| JP | 10-335092 A | 12/1998 |
| JP | 2000-175895 A | 6/2000 |
| JP | 2002-263097 A | 9/2002 |
| JP | 2003-135445 A | 5/2003 |
| JP | 2003-209746 A | 7/2003 |
| JP | 2003-260047 A | 9/2003 |
| JP | 2003-265459 A | 9/2003 |
| JP | 2003-310599 A | 11/2003 |
| JP | 2005-058774 A | 3/2005 |
| JP | 2005-073765 A | 3/2005 |
| JP | 2005-143759 A | 6/2005 |
| JP | 2005-168870 A | 6/2005 |
| JP | 2005-261838 A | 9/2005 |

\* cited by examiner

F I G. 12
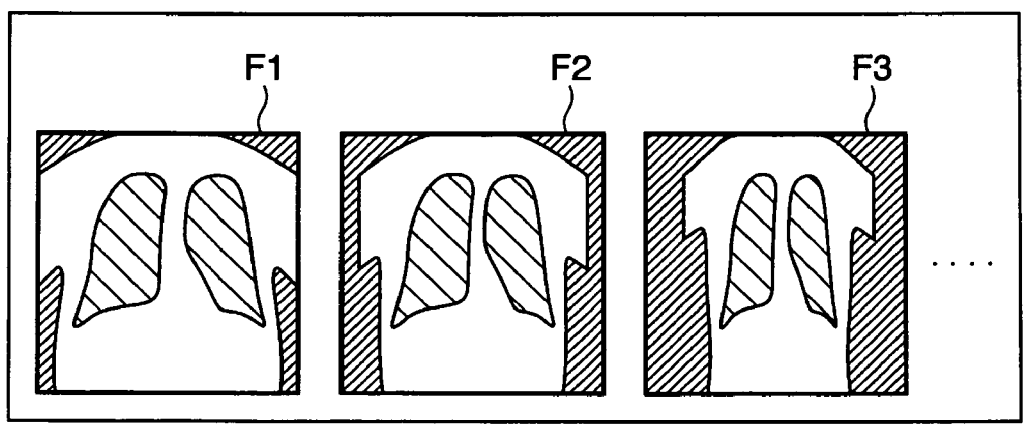

US 7,978,816 B2

RADIOGRAPHIC IMAGING CONTROL APPARATUS USING MULTI RADIATION GENERATING APPARATUS

TECHNICAL FIELD

The present invention relates to a radiographic imaging control apparatus using a multi radiation generating apparatus and a control method thereof.

BACKGROUND ART

To acquire digital data of a large screen, a two-dimensional X-ray sensor (FPD: Flat Panel Detector) for X-ray imaging has been developed recently. In particular, an imaging apparatus using a two-dimensional X-ray sensor having a large light-receiving surface with a size of 43 cm×43 cm has been put in practical use for simple imaging.

Additionally, a CT apparatus for acquiring three-dimensional image data by using a two-dimensional X-ray sensor has been developed. In this CT apparatus, the two-dimensional X-ray sensor receives an X-ray beam that is called a cone beam and has a three-dimensional extent.

When a cone beam is used, the range of patient imaging by scanning of one rotation can widen as compared to a CT apparatus using a fan beam with a two-dimensional extent. This improves the imaging efficiency.

However, it has been pointed out that an increase in the cone angle in the Z-axis direction of X-ray irradiation increases the influence of scattering rays and errors in reconstruction calculations, resulting in degradation of image quality.

A conventional radiographic imaging technique for a still image is disclosed in Japanese Patent Laid-Open No. 2003-209746. In Japanese Patent Laid-Open No. 2003-209746, when the sensor output is saturated, the estimated output in the saturation region is calculated based on the signal in the leading edge or attenuation region of the sensor output before or after the saturation. The imaging apparatus disclosed in this prior art generates image data by combining the steady output and estimated output.

As described above, the CT apparatus using a cone beam can widen the range of patient imaging by scanning within one rotation. For this reason, the number of rotations can be small, and the imaging efficiency can be increased. However, it has been pointed out that an increase in the cone angle in the Z-axis direction of X-ray irradiation increases the influence of scattering rays and errors in reconstruction calculations, resulting in degradation of image quality.

A patient has regions such as the lungs that pass X-rays well and regions such as the belly that does not pass X-rays well. The CT apparatus using a cone beam can hardly change the irradiation dose for each region.

In the method of calculating an estimated output in a saturation or overflow region, as described in Japanese Patent Laid-Open No. 2003-209746, even a slight estimation error in each projection image can largely affect a reconstructed image because of the principle of CT reconstruction.

DISCLOSURE OF INVENTION

It is an object of the present invention to provide a control apparatus capable of solving the above-described problems, suppressing degradation in image quality due to an increase in the cone angle, and setting an appropriate irradiation dose for each region of a patient, and a control method thereof.

It is another object of the present invention to provide a control apparatus that suppresses the influence of radiation from an adjacent radiation generating device.

In order to achieve at least one of the above-described objects, according to an aspect of the present invention, there is provided a control apparatus for controlling a multi radiation generating apparatus having a plurality of radiation generating devices which irradiate a two-dimensional sensor with radiation, comprising: an input device which inputs information about a part of a patient; and a controller which controls the multi radiation generating apparatus on the basis of the information about the part of the patient, which is input by the input device.

According to another aspect, there is provided a control apparatus for controlling a multi radiation generating apparatus having a plurality of radiation generating devices which irradiate a two-dimensional sensor with radiation, comprising: an input device which inputs information about a physique of a patient; and a controller which controls the multi radiation generating apparatus on the basis of the information about the physique of the patient, which is input by the input device.

According to still another aspect, there is provided a control apparatus for controlling a multi radiation generating apparatus having a plurality of radiation generating devices which irradiate a two-dimensional sensor with radiation, comprising: an input device which inputs a radiation irradiation indication; and a controller which controls radiation irradiation by the plurality of radiation generating devices by inhibiting radiation irradiation by both of adjacent radiation generating devices of the plurality of radiation generating devices at a given time in accordance with the radiation irradiation indication.

Further features of the present invention will become apparent from the following description of exemplary embodiments (with reference to the attached drawings).

BRIEF DESCRIPTION OF DRAWINGS

FIG. 12 is an explanatory view of the frames of a projection image;

BEST MODE FOR CARRYING OUT THE INVENTION

Preferred embodiments of the present invention will be described below.

The present invention will be described in detail based on the illustrated embodiments.

First Embodiment

Figure 1:
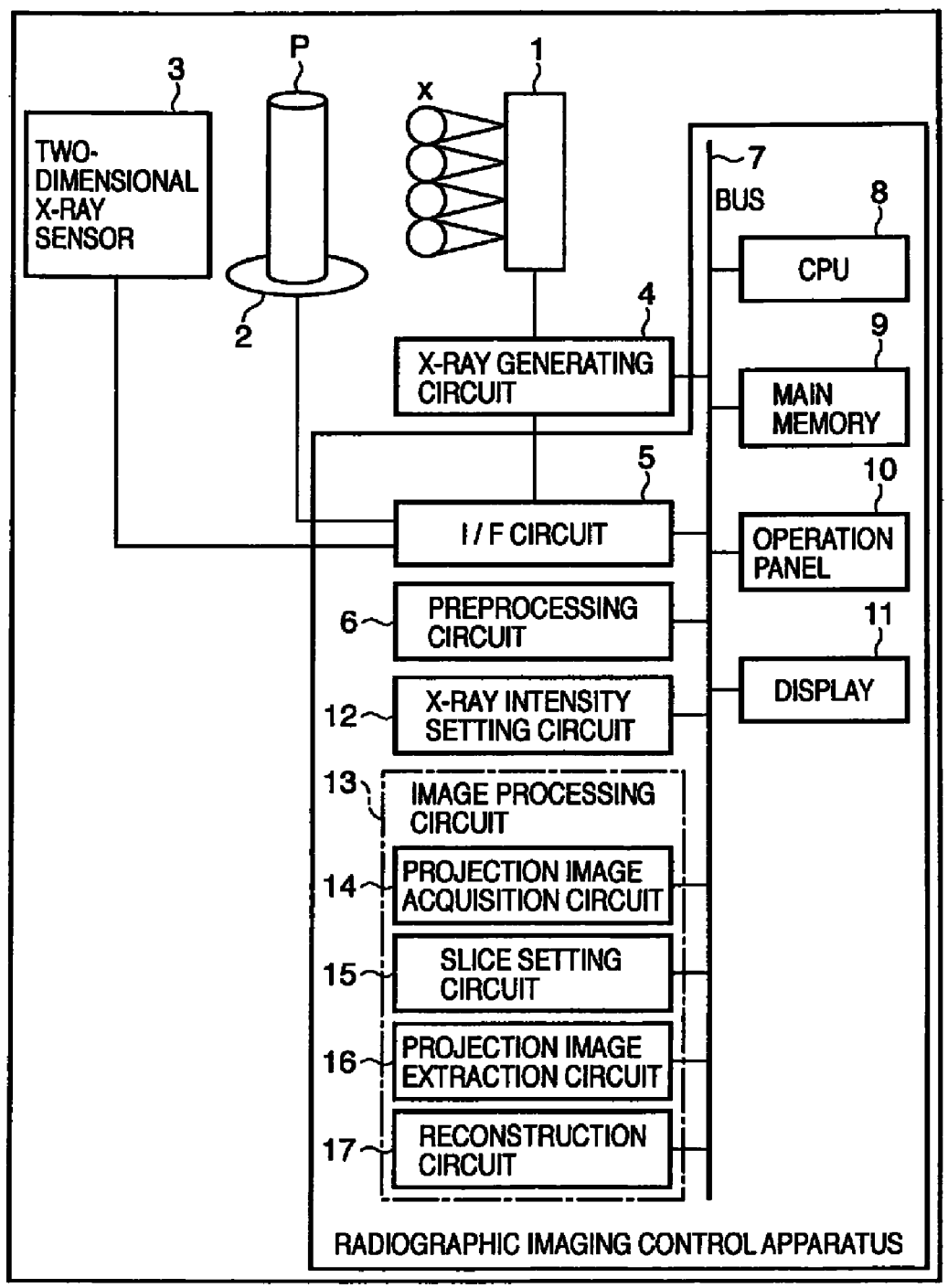
FIG. 1 is a view showing the arrangement of a system according to the first embodiment.

FIG. 1 shows a system including a radiographic imaging control apparatus according to the first embodiment. A multi X-ray generating apparatus 1 including a plurality of X-ray generating devices which are one-dimensionally arranged irradiates a two-dimensional X-ray sensor 3 with an X-ray beam x that is radiation. The X-ray beam x passes through a patient (object) P on a rotating apparatus 2 and reaches the two-dimensional X-ray sensor 3 serving as a two-dimensional radiation detection sensor. The X-ray beam x is a cone beam having a three-dimensional extent.

An X-ray generating circuit 4 is incorporated in or connected to the multi X-ray generating apparatus 1. The X-ray generating circuit 4 is connected to an interface circuit 5. The interface circuit 5 is connected to the rotating apparatus 2 and two-dimensional X-ray sensor 3. The interface circuit 5 is also connected to a bus 7.

A CPU 8 serving as controller, a main memory 9, an operation panel 10, a display 11, an X-ray intensity setting circuit 12, and an image processing circuit 13 are connected to the bus 7. These units can mutually exchange data through the bus 7. The image processing circuit 13 includes a projection image acquisition circuit 14, slice setting circuit 15, projection image extraction circuit 16, and reconstruction circuit 17. These circuits are connected to the bus 7.

In this radiographic imaging control apparatus, the main memory 9 stores various kinds of data necessary for processes in the CPU 8. The main memory 9 also stores a program that is executed by the CPU 8 to control the respective circuits. The main memory 9 includes the work memory of the CPU 8. The CPU 8 controls the operation of the overall apparatus in accordance with an operation from the operation panel 10 by using the main memory 9.

Figure 2:
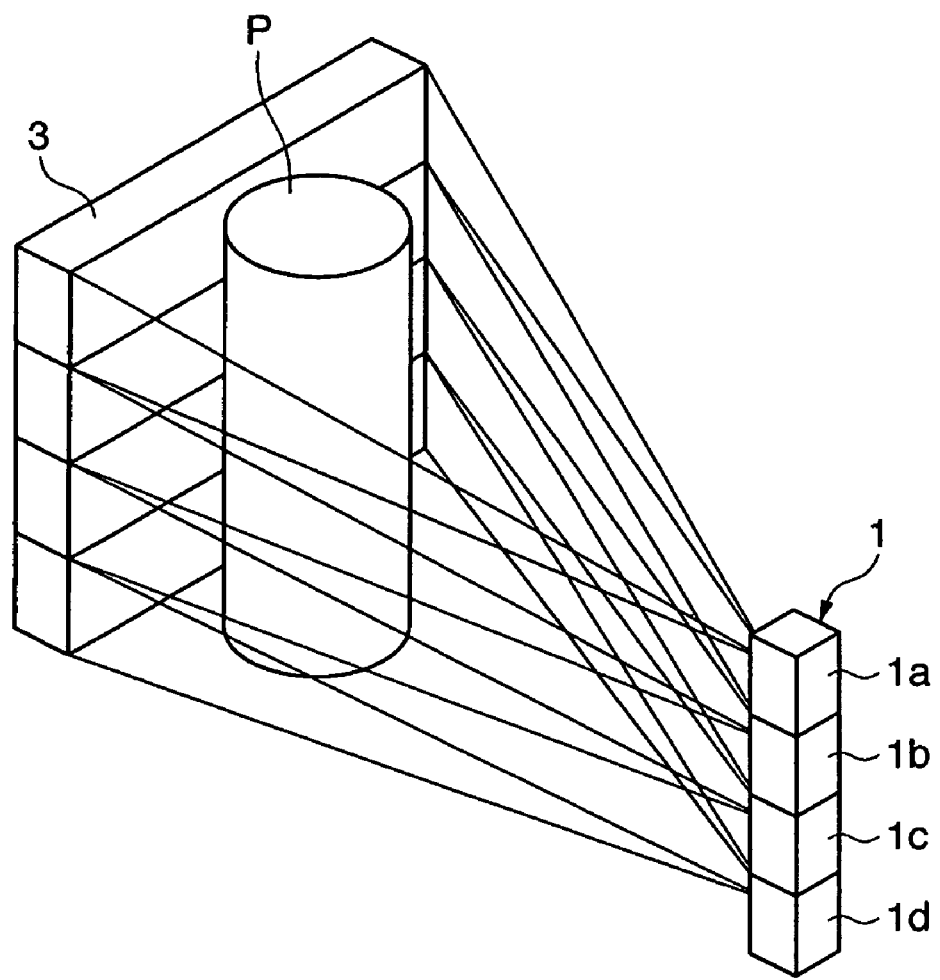
FIG. 2 is a schematic view of X-ray radiation.

As shown in FIG. 2, the multi X-ray generating apparatus 1 includes X-ray generating devices 1a to 1d which are one-dimensionally arranged. Each of the X-ray generating devices 1a to 1d can individually change the intensity of X-rays for irradiation in accordance with a current supplied from the X-ray generating circuit 4. The X-ray generating circuit 4 determines the current value to be supplied to the X-ray generating devices 1a to 1d on the basis of a control instruction from the CPU 8.

Figure 3:
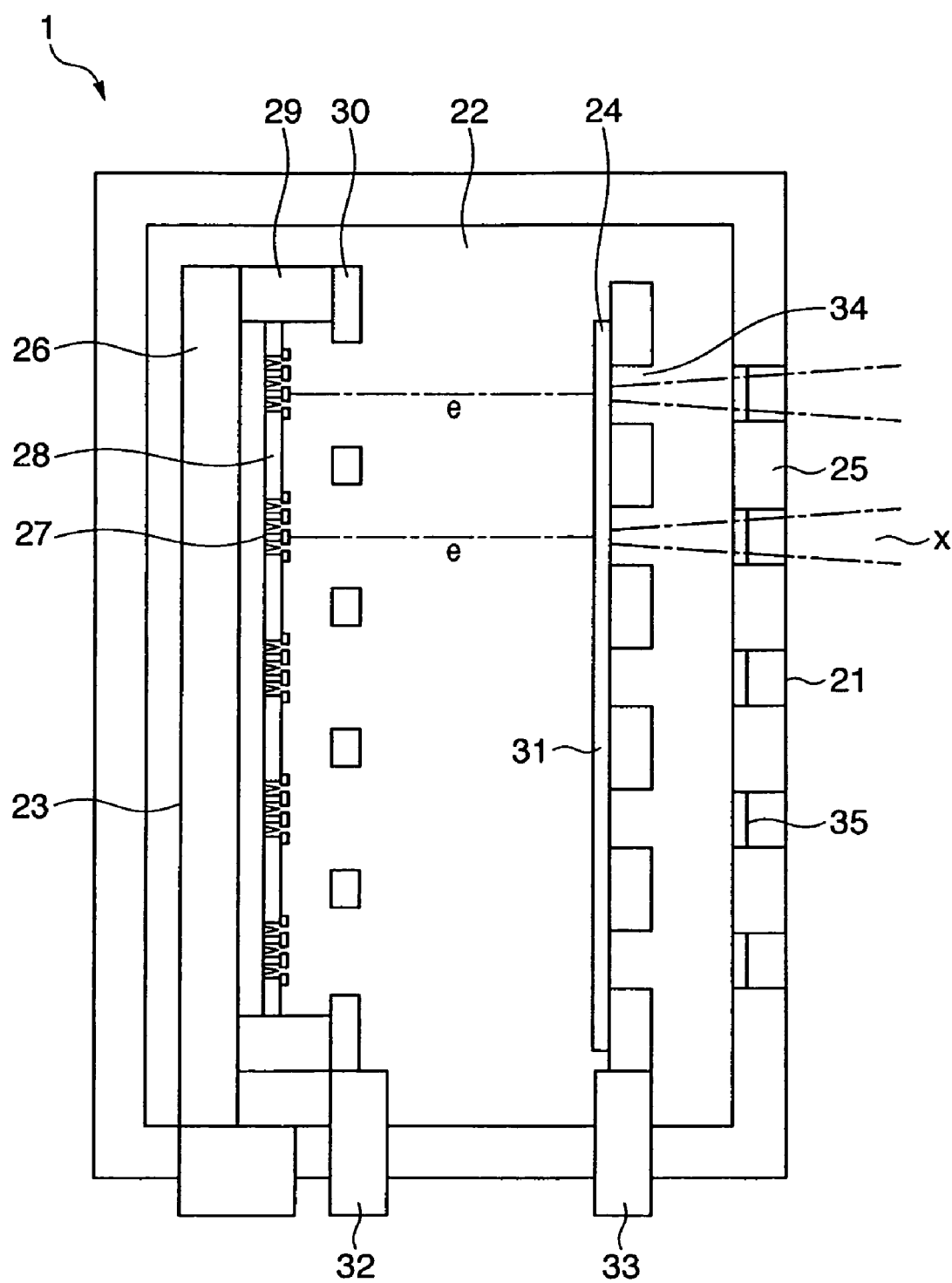
FIG. 3 is a view showing the arrangement of a multi X-ray generating apparatus.

FIG. 3 is a view showing the detailed arrangement of the multi X-ray generating apparatus 1. Referring to FIG. 3, the X-ray beam x exits from each of X-ray extraction windows 21. In this example, five X-ray extraction windows 21 exist. However, the number of windows may be 4, as in the multi X-ray generating apparatus 1 shown in FIG. 2. A multi electron beam generating portion 23 in a vacuum chamber 22 of the multi X-ray generating apparatus 1 generates a plurality of electron beams e. The electron beams e irradiate an anode electrode 24 to generate X-rays. The X-rays generated in the vacuum chamber 22 are radiated into air through the X-ray extraction windows 21 formed in a vacuum wall 25 as the X-ray beams x of multi X-ray beams.

The multi electron beam generating portion 23 includes a multi electron beam element substrate 26 and a multi electron beam element array 28 with multi electron beam elements 27 being arrayed on it. Each electron beam e extracted from the multi electron beam element array 28 receives the lens effect of a lens electrode 30 fixed to an insulating member 29 and is accelerated to the final potential level at the portion of a transmission target 31 of the anode electrode 24. High-voltage introducing portions 32 and 33 supply a high voltage to the lens electrode 30 and anode electrode 24, respectively. The transmission targets 31 are discretely arranged in correspondence with the multi electron beams e. X-rays generated at the transmission targets 31 pass through X-ray extraction portions 34 and are radiated into air from the X-ray extraction windows 21 having X-ray transmission films 35.

At the start of execution of imaging using the radiographic imaging control apparatus, the CPU 8 controls the X-ray intensity setting circuit 12 to set X-ray intensities in accordance with the imaged part intensity setting circuit 12 refers to an intensity setting table stored in its internal memory and sets the output current intensity of each of the X-ray generating devices 1a to 1d of the multi X-ray generating apparatus 1 in correspondence with the imaged part information and physique information (size information) of the patient (object) P. The imaged part information and physique information (size information) of the patient (object) P are input through the operation panel 10.

The main memory 9 holds information (current values) about the X-ray output intensities set by the X-ray intensity setting circuit 12. The memory in the X-ray intensity setting circuit 12 holds an intensity table as shown in, for example, Table 1.

TABLE 1

| | Physique | | |
|---|---|---|---|
| | Physique smaller than standard | Standard physique | Physique larger than standard |
| Imaged Part | | Head | |
| | 1a: 0 mA | 1a: 0 mA | 1a: 0 mA |
| | 1b: 10 mA | 1b: 15 mA | 1b: 20 mA |
| | 1c: 10 mA | 1c: 15 mA | 1c: 20 mA |
| | 1d: 0 mA | 1d: 0 mA | 1d: 0 mA |
| Imaged Part | | Head to Chest | |
| | 1a: 10 mA | 1a: 15 mA | 1a: 20 mA |
| | 1b: 10 mA | 1b: 15 mA | 1b: 20 mA |
| | 1c: 8 mA | 1c: 10 mA | 1c: 15 mA |
| | 1d: 8 mA | 1d: 10 mA | 1d: 15 mA |
| Imaged Part | | Chest | |
| | 1a: 8 mA | 1a: 10 mA | 1a: 15 mA |
| | 1b: 8 mA | 1b: 10 mA | 1b: 15 mA |
| | 1c: 8 mA | 1c: 10 mA | 1c: 15 mA |
| | 1d: 10 mA | 1d: 15 mA | 1d: 20 mA |
| Imaged Part | | Chest to Belly | |
| | 1a: 8 mA | 1a: 10 mA | 1a: 15 mA |
| | 1b: 8 mA | 1b: 10 mA | 1b: 15 mA |
| | 1c: 10 mA | 1c: 15 mA | 1c: 20 mA |
| | 1d: 15 mA | 1d: 20 mA | 1d: 30 mA |
| Imaged Part | | Belly | |
| | 1a: 10 mA | 1a: 15 mA | 1a: 20 mA |
| | 1b: 15 mA | 1b: 20 mA | 1b: 30 mA |
| | 1c: 15 mA | 1c: 20 mA | 1c: 30 mA |
| | 1d: 15 mA | 1d: 20 mA | 1d: 30 mA |

For example, when the imaged part is "chest to belly", and the patient has a standard physique, the CPU 8 sets the current value to be supplied to the first X-ray generating device 1a to 10 mA, the current value to be supplied to the second X-ray generating device 1b to 10 mA, the current value to be supplied to the third X-ray generating device 1c to 15 mA, and the current value to be supplied to the fourth X-ray generating device 1d to 20 mA. That is, according to this embodiment, it is possible to simultaneously obtain images of a plurality of parts for which the appropriate X-ray intensities are different.

For example, when the imaged part is "head", irradiation using the X-ray generating devices 1a and 1d, which irradiate parts except the head, is inhibited. That is, since X-ray irradiation by X-ray generating devices, which irradiate parts except the imaged part, is restricted, the X-ray irradiation coverage can be limited without using a member such as an irradiation iris.

The imaged part information and physique information can be input manually by, for example, the operator through the operation panel 10. In this case, the operation panel 10 serves as an input device. It is also possible to input these pieces of information from an imaging inspection order system connected to the radiographic imaging control apparatus through a network. In this case, a network interface (not shown) serves as an input device.

The physique information (size information) of the patient (object) P may be acquired from the outline information of the patient (object) P, which is obtained by taking an image of the patient (object) P by using a camera (not shown). The imaged part information may be acquired from the shape of the imaged part, which is obtained by taking an image of the imaged part of the patient (object) P placed on the two-dimensional X-ray sensor 3 by using a camera (not shown). In this case, an interface (e.g., interface circuit 5) connected to the camera serves as an input device.

The CPU 8 detects these input signals and controls the X-ray intensity setting circuit 12 such that the output intensities of the X-ray generating devices 1a to 1d of the multi X-ray generating apparatus 1 are set in the main memory 9 in correspondence with the detected input signals by referring to Table 1. Note that in imaging an object whose size is defined in advance, only imaged part information needs to be set.

Next, the CPU 8 activates the rotating apparatus 2 through the interface circuit 5, thereby rotating the patient P. Based on an instruction from the CPU 8, the X-ray generating circuit 4 emits, to the patient P, the X-ray beams x with the output intensities set by the X-ray intensity setting circuit 12 while sequentially switching the four X-ray generating devices 1a to 1d of the multi X-ray generating apparatus 1. The X-ray beams x radiated from the multi X-ray generating apparatus 1 pass through the patient P while attenuating and reach the two-dimensional X-ray sensor 3. The two-dimensional X-ray sensor 3 obtains a projection image by converting the radiation into an electrical signal.

Figure 4A:
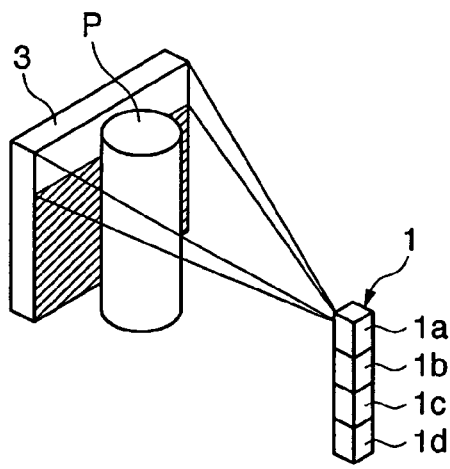
FIGS. 4A to 4D are explanatory views of an X-ray generating device switching order.
Figure 4B:
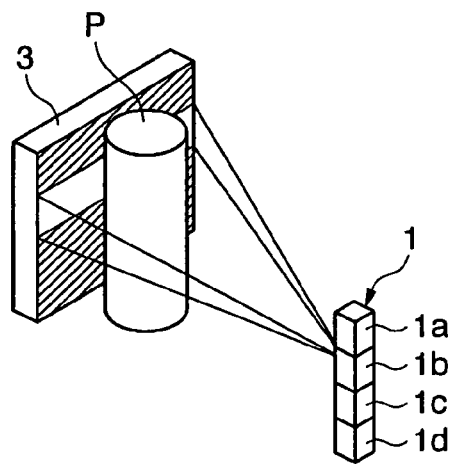
Figure 4C:
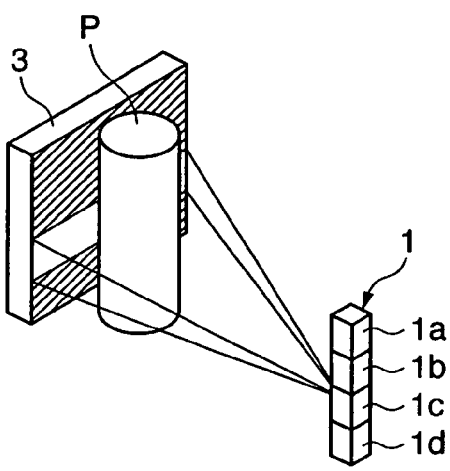
Figure 4D:
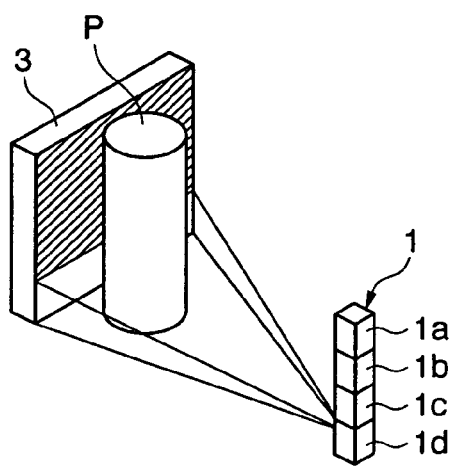

In this embodiment, the switching order of the X-ray generating devices 1a to 1d of the multi X-ray generating apparatus 1 is set as in, for example, FIGS. 4A, 4B, 4C, 4D, 4A, 4B, ..., as described above. FIG. 4A shows a state wherein the X-ray generating device 1a emits X-rays. FIG. 4B shows a state wherein the X-ray generating device 1b emits X-rays. FIG. 4C shows a state wherein the X-ray generating device 1c emits X-rays. FIG. 4D shows a state wherein the X-ray generating device 1d emits X-rays.

Figure 5A:
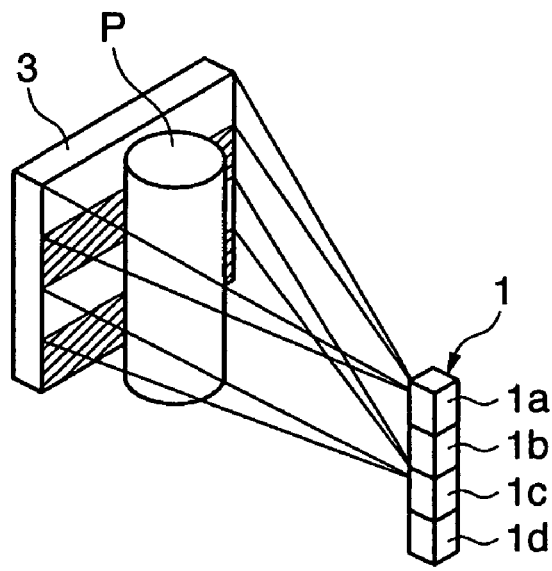
FIGS. 5A and 5B are explanatory views of another X-ray generating device switching order.
Figure 5B:
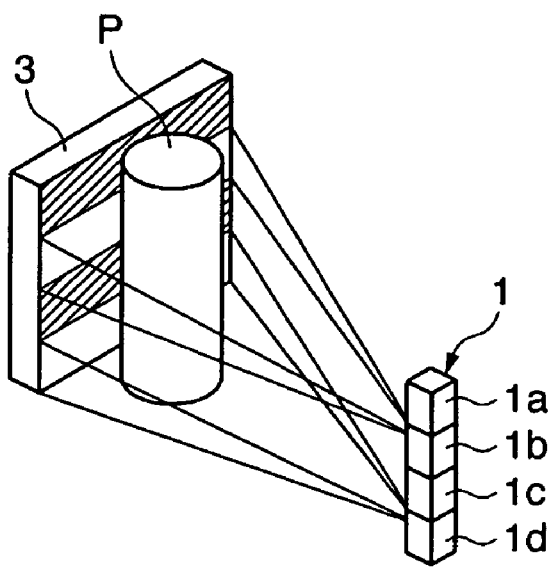

To further increase the efficiency, the plurality of X-ray generating devices 1a to 1d may be used simultaneously. However, when two adjacent ones of the X-ray generating devices 1a to 1d are used simultaneously, the X-rays that have reached the two-dimensional X-ray sensor 3 form an overlap region and complicate the correction of projection image data. Alternatively, the X-rays may exceed the dynamic range of the X-ray sensor 3. To prevent simultaneous use of at least two adjacent ones of the X-ray generating devices 1a to 1d, the X-ray irradiation order is preferably set as shown in FIGS. 5A, 5B, 5A, 5B . . . . FIG. 5A shows a state wherein the X-ray generating devices 1a and 1c emit X-rays. FIG. 5B shows a state wherein the X-ray generating devices 1b and 1d emit X-rays.

The interface circuit 5 supplies, to a preprocessing circuit 6, the projection image output from the two-dimensional X-ray sensor 3. The preprocessing circuit 6 executes preprocesses such as offset correction and gain correction for the projection image. The projection image that has undergone the preprocesses by the preprocessing circuit 6 is transferred to the main memory 9 and image processing circuit 13 through the bus 7 under the control of the CPU 8.

In this embodiment, the two-dimensional X-ray sensor 3 and preprocessing circuit 6 are separated. However, the two-dimensional X-ray sensor 3 and preprocessing circuit 6 may be formed in a single sensor unit.

The CPU 8 controls the multi X-ray generating apparatus 1 through the X-ray generating circuit 4 to emit the X-ray beam x while driving the rotating apparatus 2 to rotate the patient P and sequentially switching the X-ray generating devices 1a to 1d. In this operative state, that is, CT scanning state, the two-dimensional X-ray sensor 3 successively acquires projection images and sequentially outputs the acquired projection images to the interface circuit 5. For example, the two-dimensional X-ray sensor 3 outputs 1,000 projection images while the patient P rotates 360°. These projection images are input to the preprocessing circuit 6 through the interface circuit 5. The preprocessing circuit 6 executes the above-described processes for the projection images and outputs the processed projection images to the image processing circuit 13 and main memory 9. This imaging operation allows obtaining satisfactory X-ray images taken from different directions by using the plurality of X-ray generating devices 1a to 1d.

The projection image acquisition circuit 14 in the image processing circuit 13 sequentially acquires the projection images processed by the preprocessing circuit 6 during CT scanning. The slice setting circuit 15 sets a patient region as a CT reconstruction target based on an input from the operation panel 10. The projection image extraction circuit 16 extracts projection images to be used for CT reconstruction based on the patient region set by the slice setting circuit 15. The reconstruction circuit 17 reconstructs a CT image from the plurality of extracted projection images.

Figure 6:
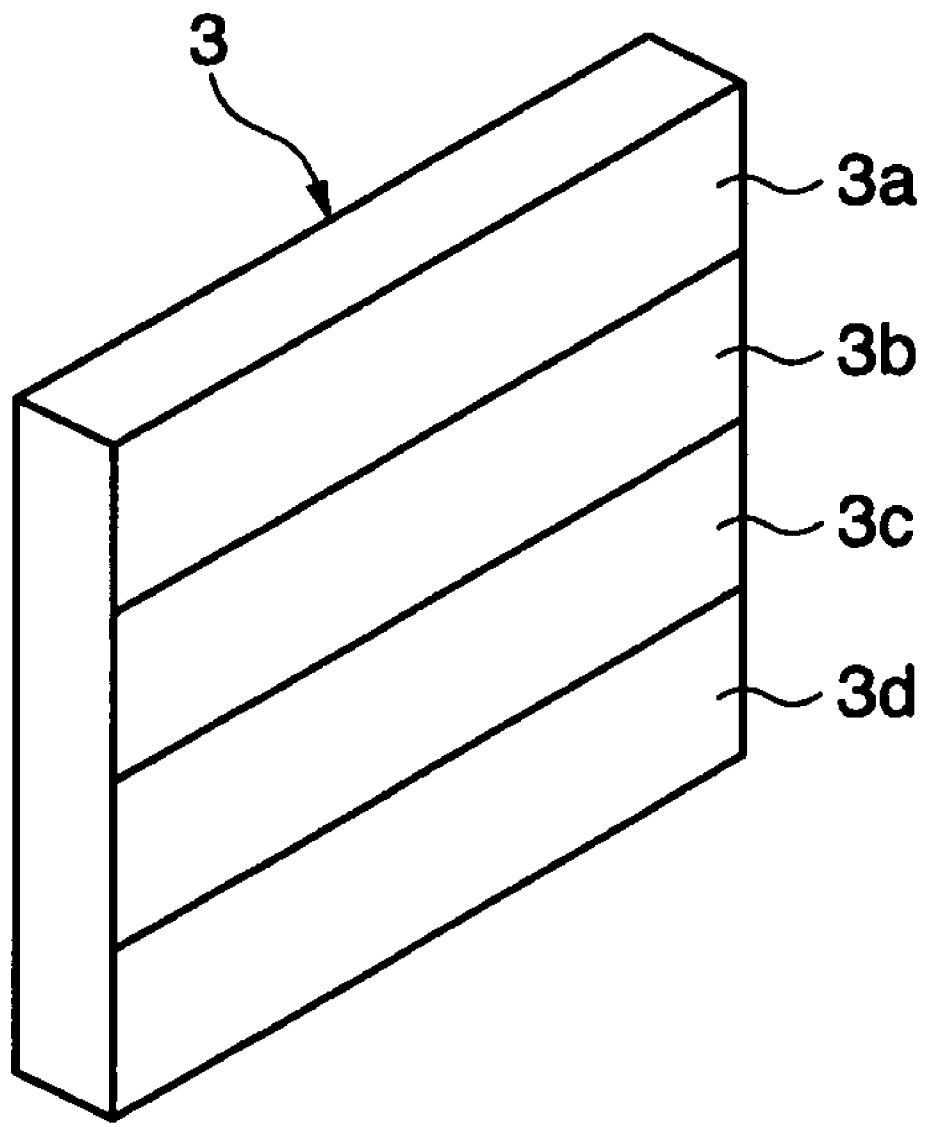
FIG. 6 is an explanatory view of the imaging region of a two-dimensional X-ray sensor.
Figure 7:
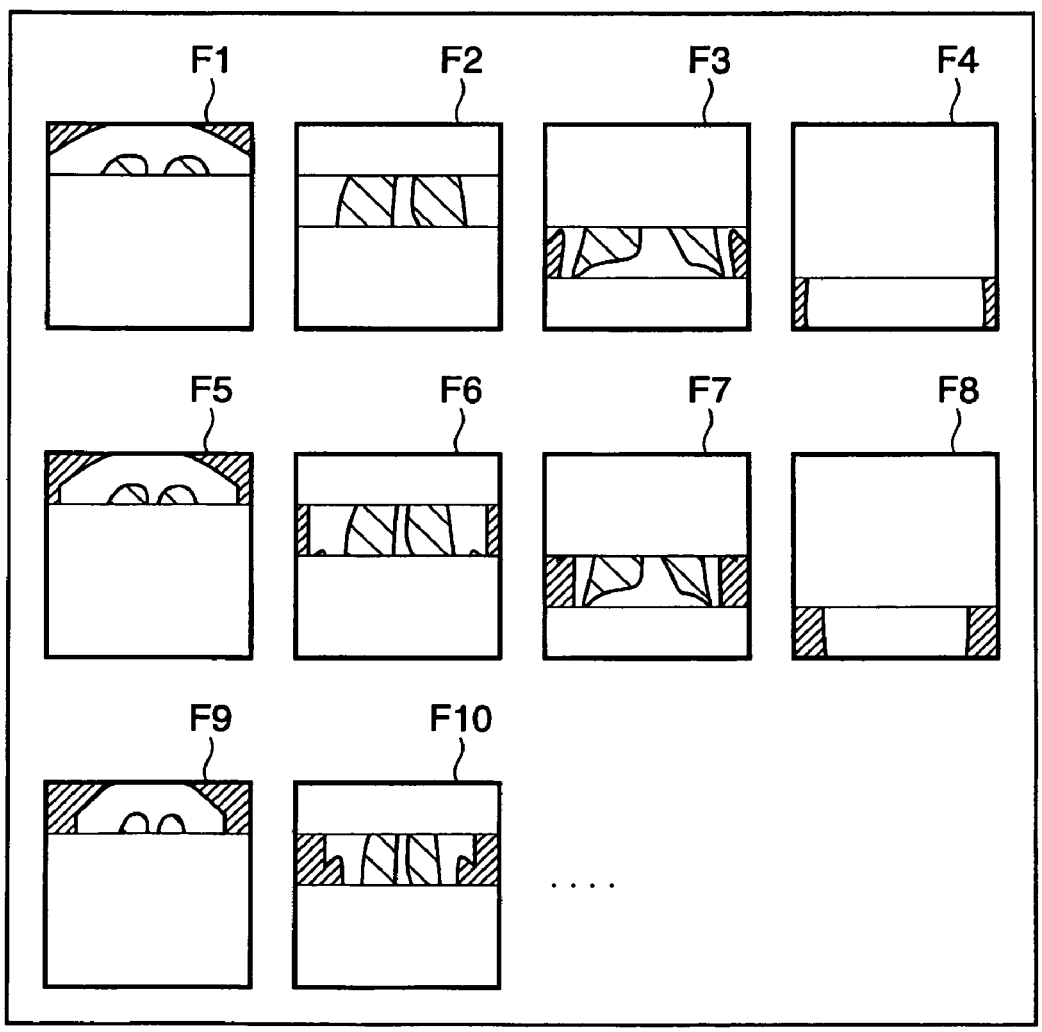
FIG. 7 is an explanatory view of the frames of a projection image.
Figure 8:
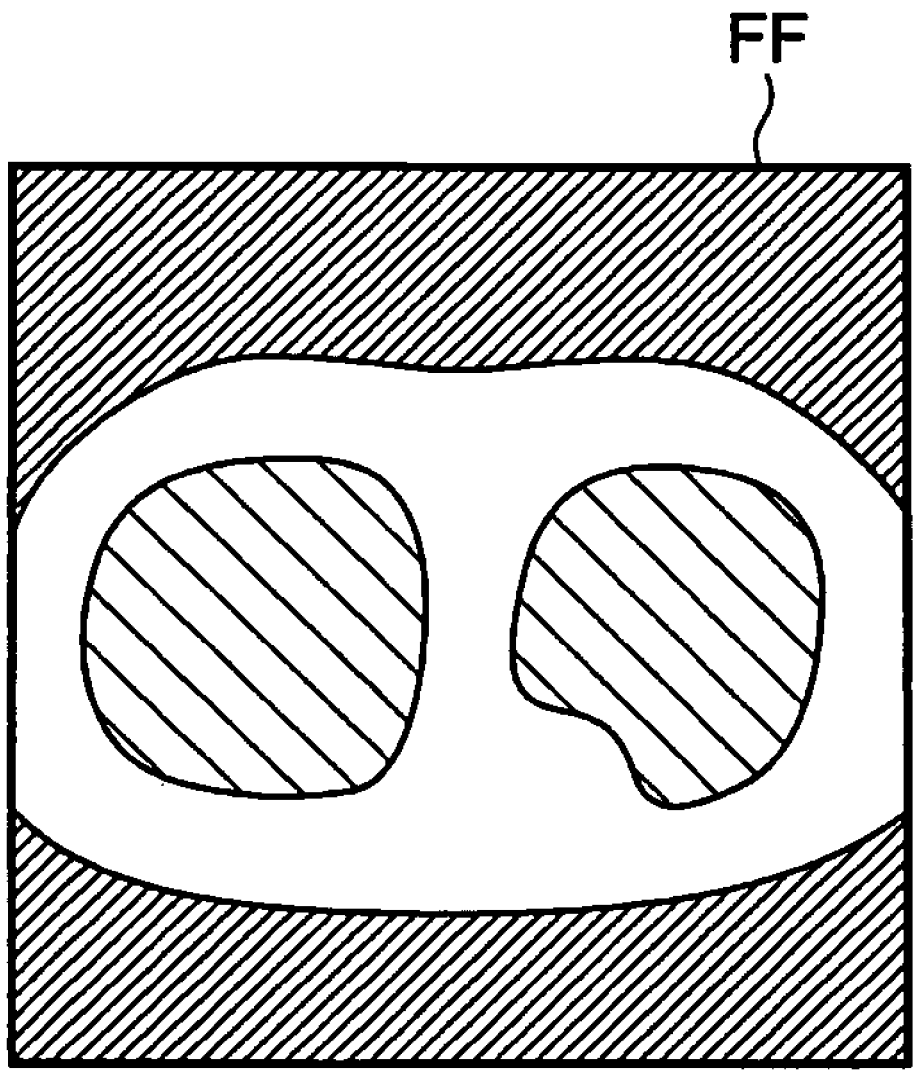
FIG. 8 is an explanatory view of a CT image.

Referring to FIG. 6, the X-ray beams x emitted from the X-ray generating devices 1a, 1b, 1c, and 1d reach first, second, third, and fourth imaging areas (pixels) 3a, 3b, 3c, and 3d of the two-dimensional X-ray sensor 3, respectively. Referring to FIG. 7, frames F1 to F4 of projection images indicate images sequentially acquired by causing the X-ray generating devices 1a to 1d to irradiate the patient P with X-rays during CT scanning. An image FF shown in FIG. 8 is a CT image reconstructed by the CT reconstruction process.

Figure 9:
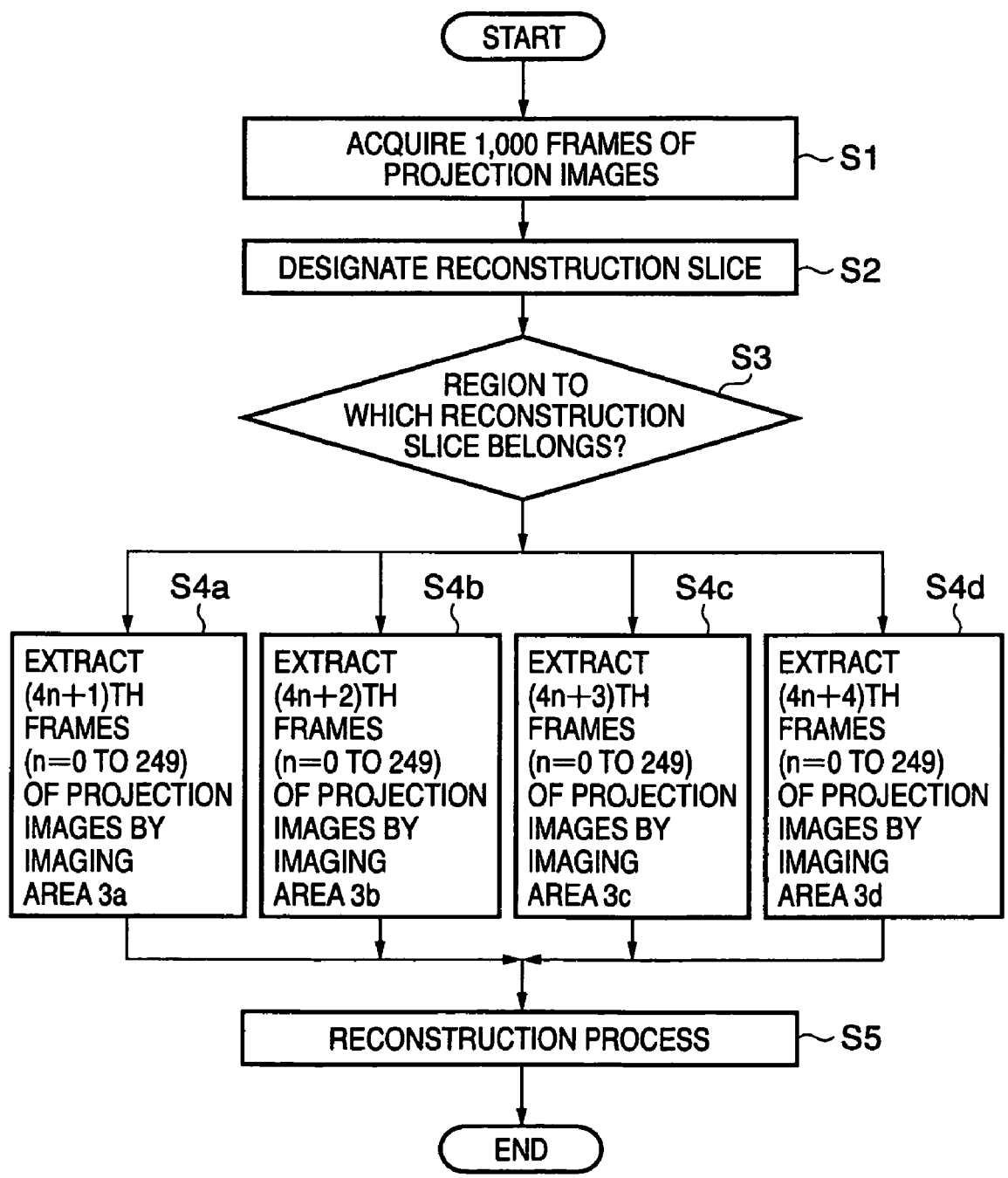
FIG. 9 is a flowchart illustrating image processing of a radiographic imaging control apparatus.

FIG. 9 is a flowchart illustrating the operation process of the image processing circuit 13. The program codes of this flowchart are stored in the main memory 9 or ROM (not shown), and read out and executed by the CPU 8.

First, the CPU 8 receives an imaging start instruction (X-ray irradiation indication) from the operation panel 10 serving as an input device. CT scanning is executed in accordance with the imaging start instruction, and the projection image acquisition circuit 14 acquires, through the bus 7, the first frame F1 of the projection image processed by the preprocessing circuit 6. The projection image acquisition circuit 14 then acquires the second frame F2 of the projection image in a similar manner and sequentially acquires projection images up to the 1000th frame (not shown) (step S1). While sequentially switching and controlling irradiation of the X-ray beam x by the four X-ray generating devices 1a to 1d, the projection image acquisition circuit 14 acquires projection images.

Hence, for example, the (4n+1)th frames (n=0 to 249) such as the first frame F1, fifth frame F5, and ninth frame F9 of projection images indicate projection images obtained when the first X-ray generating device 1a emits the X-ray beam x. Similarly, the (4n+2)th frames (n=0 to 249) indicate projection images obtained when the second X-ray generating device 1b emits the X-ray beam x. The (4n+3)th frames (n=0 to 249) and (4n+4)th frames (n=0 to 249) indicate projection images obtained when the third and fourth X-ray generating devices 1c and 1d emit the X-ray beam x.

Next, based on the coordinates of a slice target position input from, for example, the operation panel 10, the CPU 8 sets, in the slice setting circuit 15, a CT reconstruction process of generating a CT image corresponding to input coordinates (step S2). Note that the slice target position (range) may be input by using a pointing device on an arbitrary projection image displayed on, for example, the display 11.

The projection image extraction circuit 16 extracts projection images necessary for reconstructing the CT image FF, such as shown in FIG. 8, at the slice position set in process step S2 (steps S3 and S4).

When the slice position set in process step S2 belongs to the first imaging area 3a of the two-dimensional X-ray sensor 3, the projection image extraction circuit 16 extracts the (4n+1)th frames (n=0 to 249) such as the first frame F1 and fifth frame F5 of projection images (step S4a). When the slice position belongs to the second, third, and fourth imaging areas 3b, 3c, and 3d, the projection image extraction circuit 16 extracts the (4n+2)th frames, (4n+3)th frames, and (4n+4)th frames (n=0 to 249) of projection images (steps S4b to S4d).

Finally, the reconstruction circuit 17 reconstructs the CT image FF from the extracted projection images (step S5), and the operation of the image processing circuit 13 is ended. The method of acquiring a CT image from projection images by reconstruction is known, and a description thereof will be omitted.

In this embodiment, the patient P rotates. Instead, even when the multi X-ray generating apparatus 1 and two-dimensional X-ray sensor 3 rotate around the patient P, the same effect can be obtained.

As described above, according to the first embodiment, it is possible to irradiate the patient P at an optimum irradiation dose corresponding to each region by using the multi X-ray generating apparatus 1. Hence, an effect of reducing the radiation dose while maintaining the image quality or an effect of improving the image quality while maintaining the radiation dose can be obtained. In addition, the radiation cone angle of the X-ray beam x can be made small. It is therefore possible to reduce the influence of scattering rays and errors in reconstruction calculations and prevent degradation of image quality.

Note that the CPU 8 may execute the functions of the preprocessing circuit 6, X-ray intensity setting circuit 12, projection image acquisition circuit 14, slice setting circuit 15, projection image extraction circuit 16, and reconstruction circuit 17 shown in FIG. 1 by software.

Figure 15:
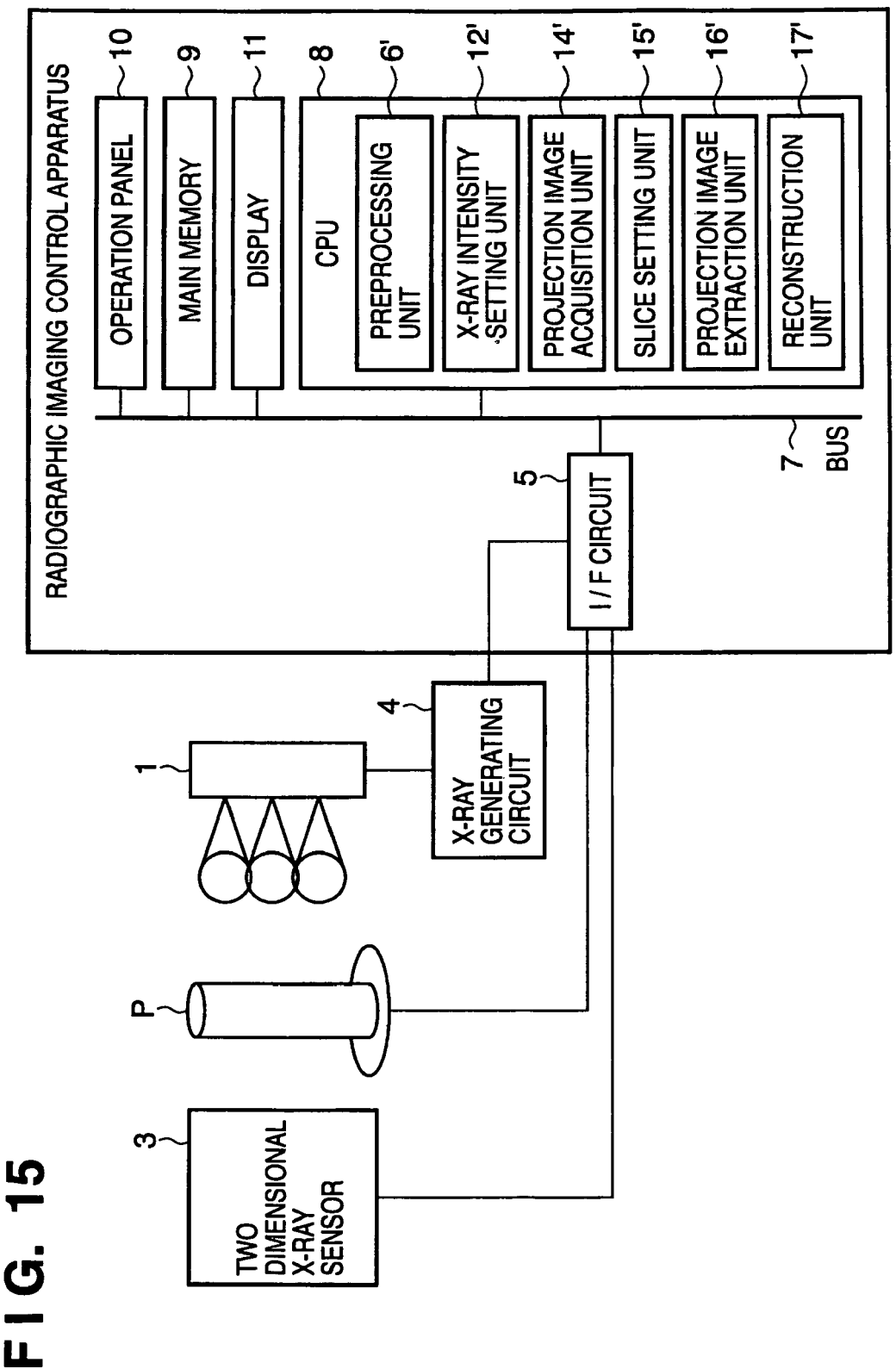
FIG. 15 is a view showing an arrangement when a radiation control apparatus is controlled using software in the system according to the first embodiment.

A radiographic imaging control apparatus shown in FIG. 15 executes the functions of the preprocessing circuit 6, X-ray intensity setting circuit 12, projection image acquisition circuit 14, slice setting circuit 15, projection image extraction circuit 16, and reconstruction circuit 17 as the functions of the CPU 8. Referring to FIG. 15, a preprocessing unit 6', X-ray intensity setting unit 12', projection image acquisition unit 14', slice setting unit 15', projection image extraction unit 16', and reconstruction unit 17' as the functions executed by the CPU 8 correspond to the preprocessing circuit 6, X-ray intensity setting circuit 12, projection image acquisition circuit 14, slice setting circuit 15, projection image extraction circuit 16, and reconstruction circuit 17 in FIG. 1, respectively. In the form shown in FIG. 15, the main memory 9 stores a program which causes the CPU 8 to execute the above-described functions.

Second Embodiment

Figure 10:
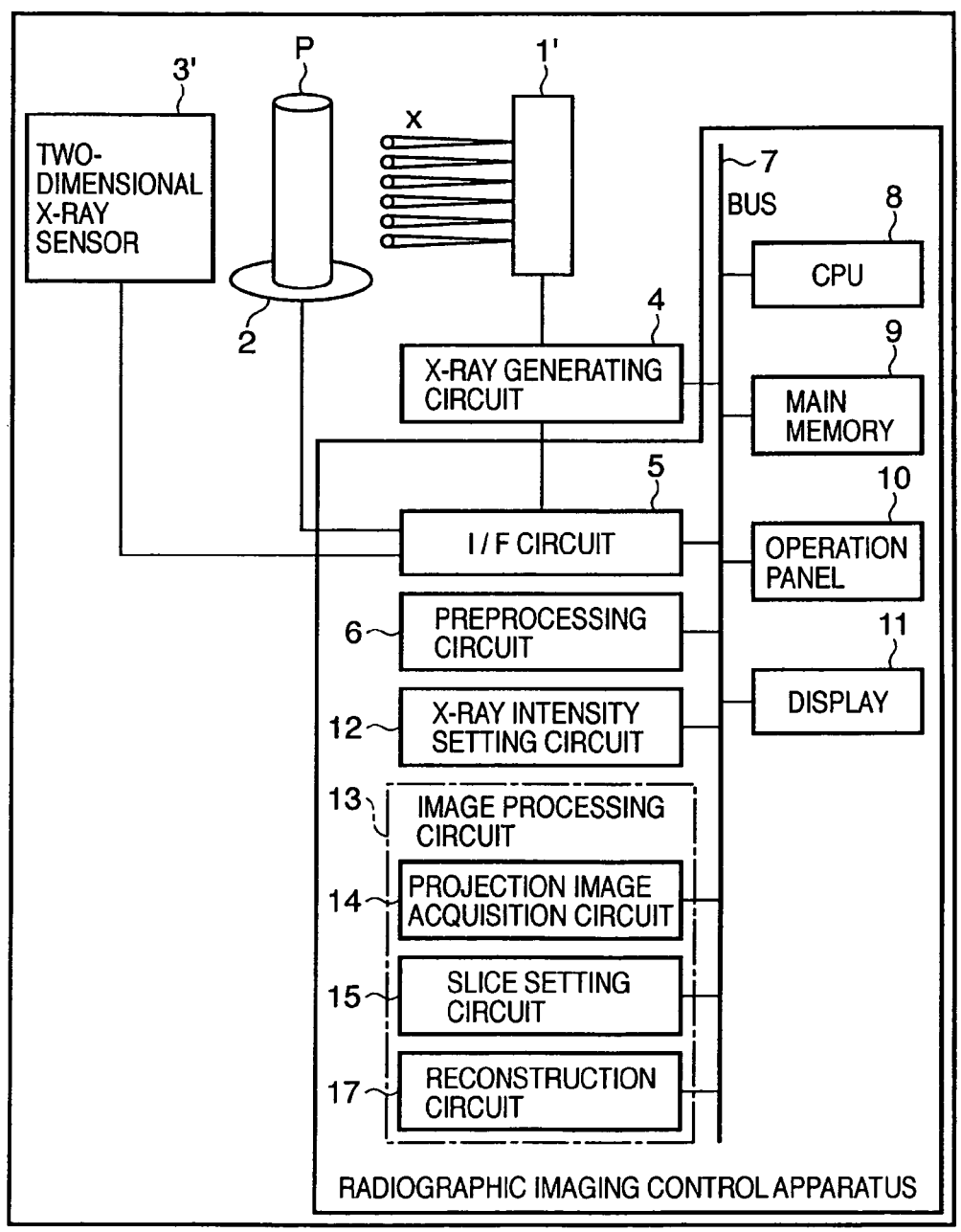
FIG. 10 is a view showing the arrangement of a system according to the second embodiment.

FIG. 10 shows the arrangement of a radiographic imaging control apparatus according to the second embodiment. The difference from the radiographic imaging control apparatus of the first embodiment is that the X-ray generating devices of a multi X-ray generating apparatus 1' are two-dimensionally arranged, and the number of X-ray sources is equal to the number of imaging areas of a two-dimensional X-ray sensor 3'. In addition, an image processing circuit 13 has no projection image extraction circuit 16.

Figure 11:
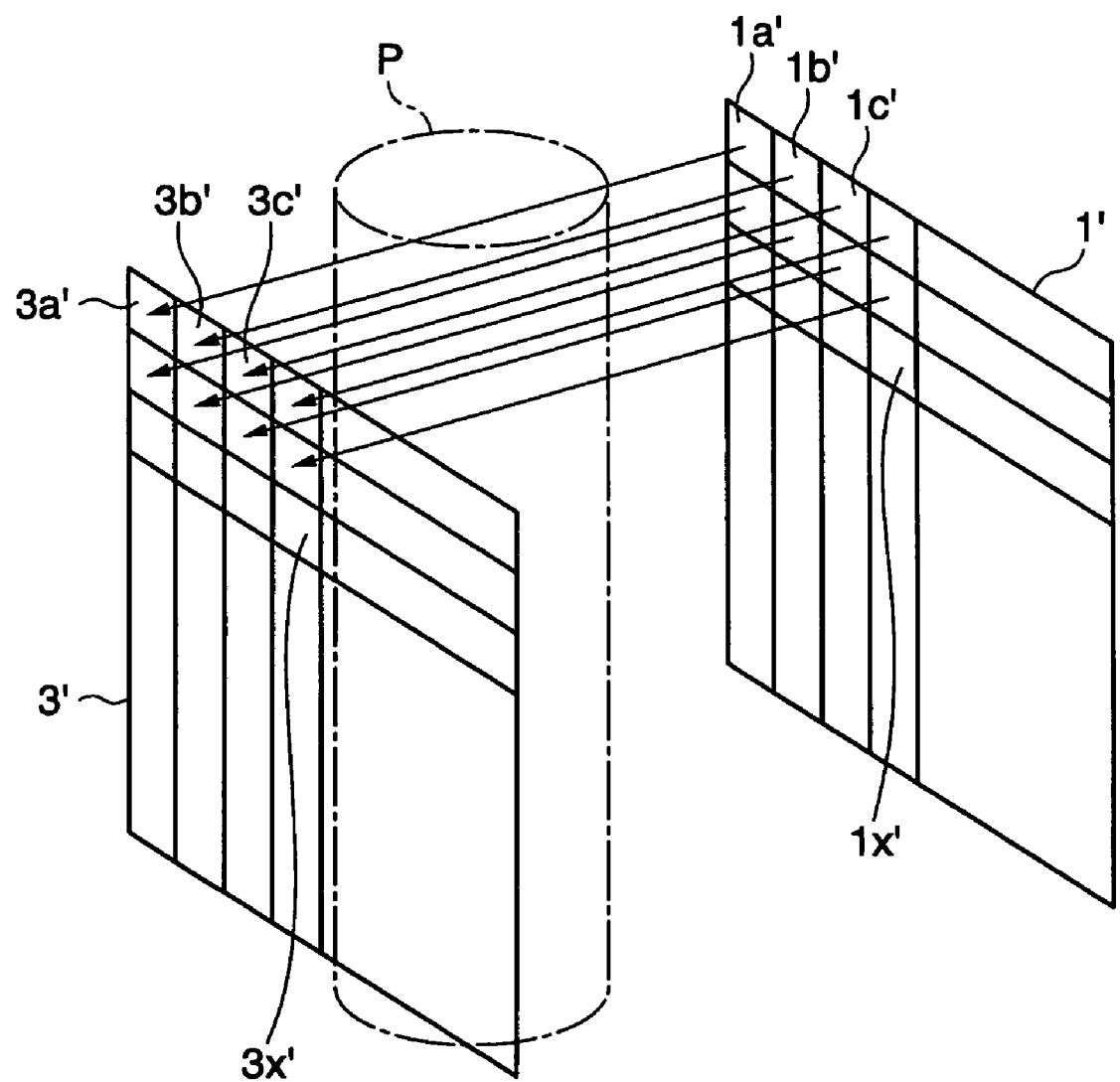
FIG. 11 is a schematic view of the correspondence between an X-ray source and the imaging region of a two-dimensional X-ray sensor.

FIG. 11 is a schematic view of the geometrical arrangement of X-ray generating devices 1a', 1b', 1c', . . . which are two-dimensionally arranged in the multi X-ray generating apparatus 1' and imaging areas 3a', 3b', 3c', . . . of the two-dimensional X-ray sensor 3'. The X-ray generating devices 1a', . . . and imaging areas 3a', . . . are in a one-to-one correspondence. Each of the X-ray generating devices 1a', 1b', . . . emits a very thin X-ray beam x, that is, pencil beam. The emitted X-ray beam x reaches a corresponding one of the imaging areas 3a', 3b', . . . of the two-dimensional X-ray sensor 3' through a patient P.

Since the X-ray generating devices 1a', 1b', . . . and opposing imaging areas 3a', 3b', . . . are in a one-to-one correspondence, the X-ray beam x need not be emitted while sequentially switching the X-ray generating devices 1a', 1b', . . . , unlike the first embodiment. Hence, all X-ray generating devices 1a', 1b', . . . can simultaneously emit the X-ray beams x to the imaging areas 3a', 3b', . . . . For this reason, each of projection images F1, F2, F3, . . . transferred from a preprocessing circuit 6 to the image processing circuit 13 includes all imaging areas, as shown in FIG. 12.

When X-ray irradiation is done by using a number of X-ray generating devices, as shown in FIG. 11, the X-ray beam irradiation coverage can easily be set in accordance with the physique of the patient P. In this case, a CPU 8 controls an X-ray intensity setting circuit 12 to set the X-ray beam irradiation coverage and intensity on the basis of the imaged part information and physique information (size information) of the patient P, which are input through an operation panel 10. The memory held in the X-ray intensity setting circuit 12 stores, as an intensity table, information about the X-ray intensity considering the X-ray beam irradiation coverage corresponding to the physique of the patient P.

Figure 14:
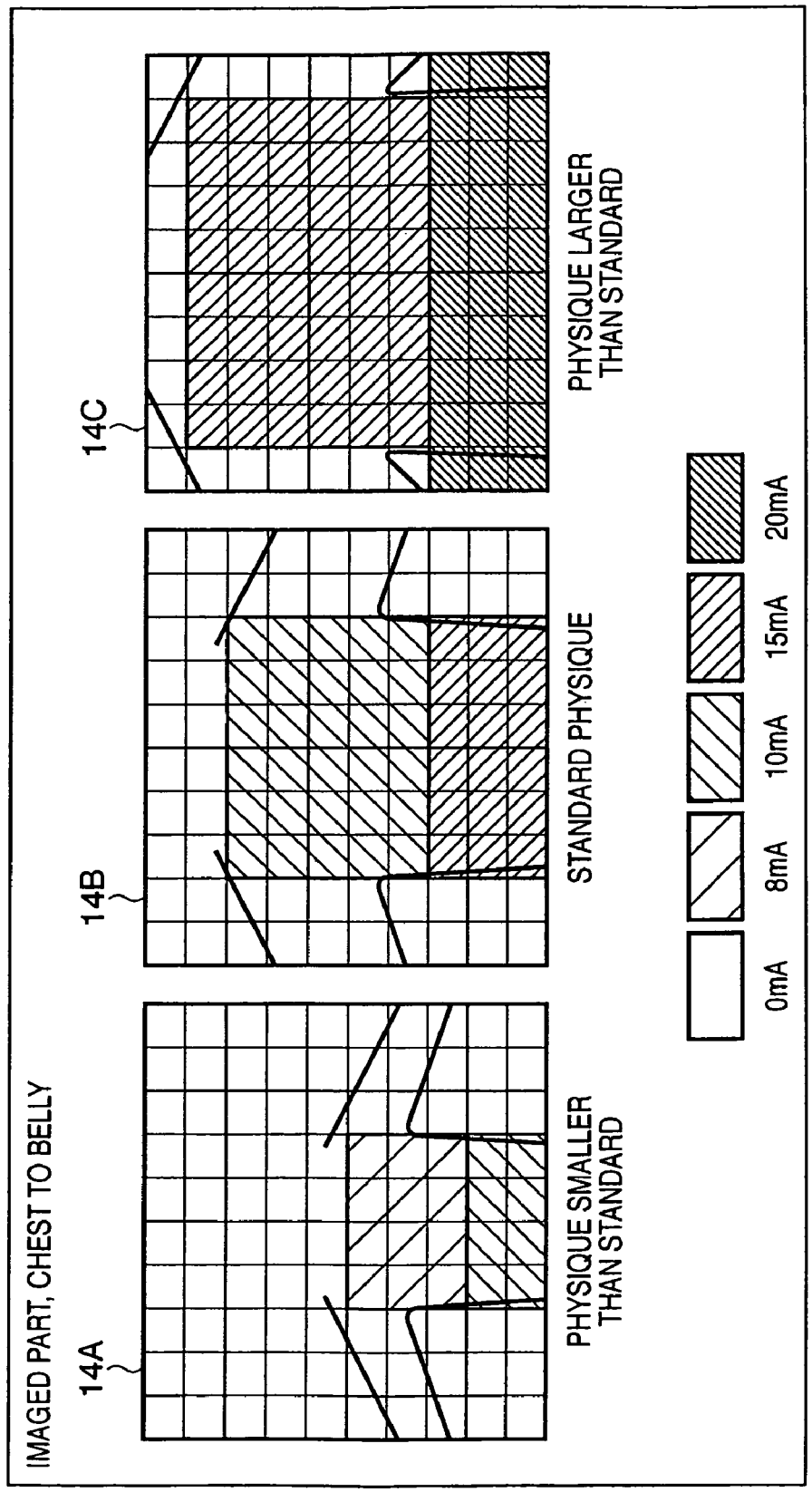
FIG. 14 is a view for explaining the intensity and irradiation coverage of X-rays corresponding to the physique of a patient.

FIG. 14 shows examples of the X-ray beam irradiation coverage and intensity set in the two-dimensional X-ray sensor 3' when the imaged part is "chest to belly". As shown in FIG. 14 by reference numbers 14A to 14C, the number of X-ray generating devices to emit X-rays is decreased as the physique of the patient P becomes small. Hence, a narrower X-ray beam irradiation coverage is set as the physique of the patient P becomes small. That is, X-ray beam irradiation by X-ray generating devices that would irradiate the area outside the range of the patient P is limited. This restricts wasteful X-ray beam irradiation. As the physique of the patient P becomes small, the intensity of the X-rays emitted from the X-ray generating devices is set to be lower.

Even for another imaged part, the memory held in the X-ray intensity setting circuit 12 stores, as an intensity table, information about the X-ray intensity considering the X-ray beam irradiation coverage corresponding to the physique of the patient P, like "chest to belly".

Figure 13:
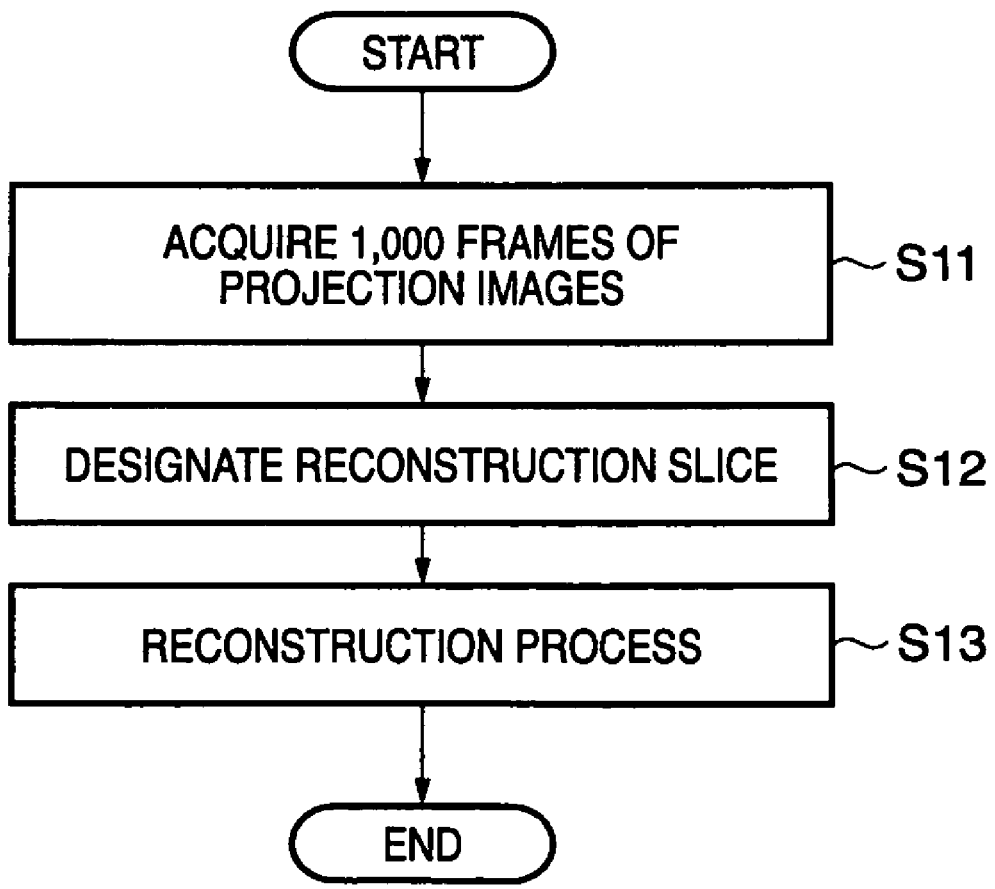
FIG. 13 is a flowchart illustrating image processing of a radiographic imaging control apparatus.

FIG. 13 is a flowchart illustrating the process of the image processing circuit 13 according to the second embodiment. When CT scanning is executed, a projection image acquisition circuit 14 in the image processing circuit 13 sequentially acquires projection images of first to 1000th frames processed by the preprocessing circuit 6 (step S11).

Next, a slice setting circuit 15 sets the coordinates of the slice position of an image to be reconstructed by CT reconstruction input from the operation panel 10 (step S12). The setting method is the same as in the first embodiment. Finally, a CT image FF is reconstructed from the projection images acquired in process step S11 by using a reconstruction circuit 17 (step S13), and the operation of the image processing circuit 13 is ended.

As described above, according to the second embodiment, equal numbers of X-ray generating devices 1a', 1b', ... and imaging areas 3a', 3b', ... of the two-dimensional X-ray sensor 3' are arranged in the same two-dimensional array. The X-ray sources and imaging areas are in a one-to-one correspondence. It is therefore possible to irradiate the patient P at an optimum irradiation dose corresponding to each region even in a direction parallel to the rotating shaft. Hence, an effect of further reducing the radiation dose while maintaining the image quality or an effect of further improving the image quality while maintaining the radiation dose can be obtained. In addition, since the X-ray beam x is an almost parallel beam, the reconstruction space (FOV) can be wider as compared to a conventional apparatus.

Note that the CPU 8 may execute the functions of the preprocessing circuit 6, X-ray intensity setting circuit 12, projection image acquisition circuit 14, slice setting circuit 15, and reconstruction circuit 17 shown in FIG. 10 by software.

Furthermore, according to the above embodiments, tube current is varied in accordance with physique as shown in the table 1 and FIG. 14. However, it is not limited to these structures. In place of tube current, or in addition to tube current, tube voltage may be varied in accordance with physique.

Figure 16:
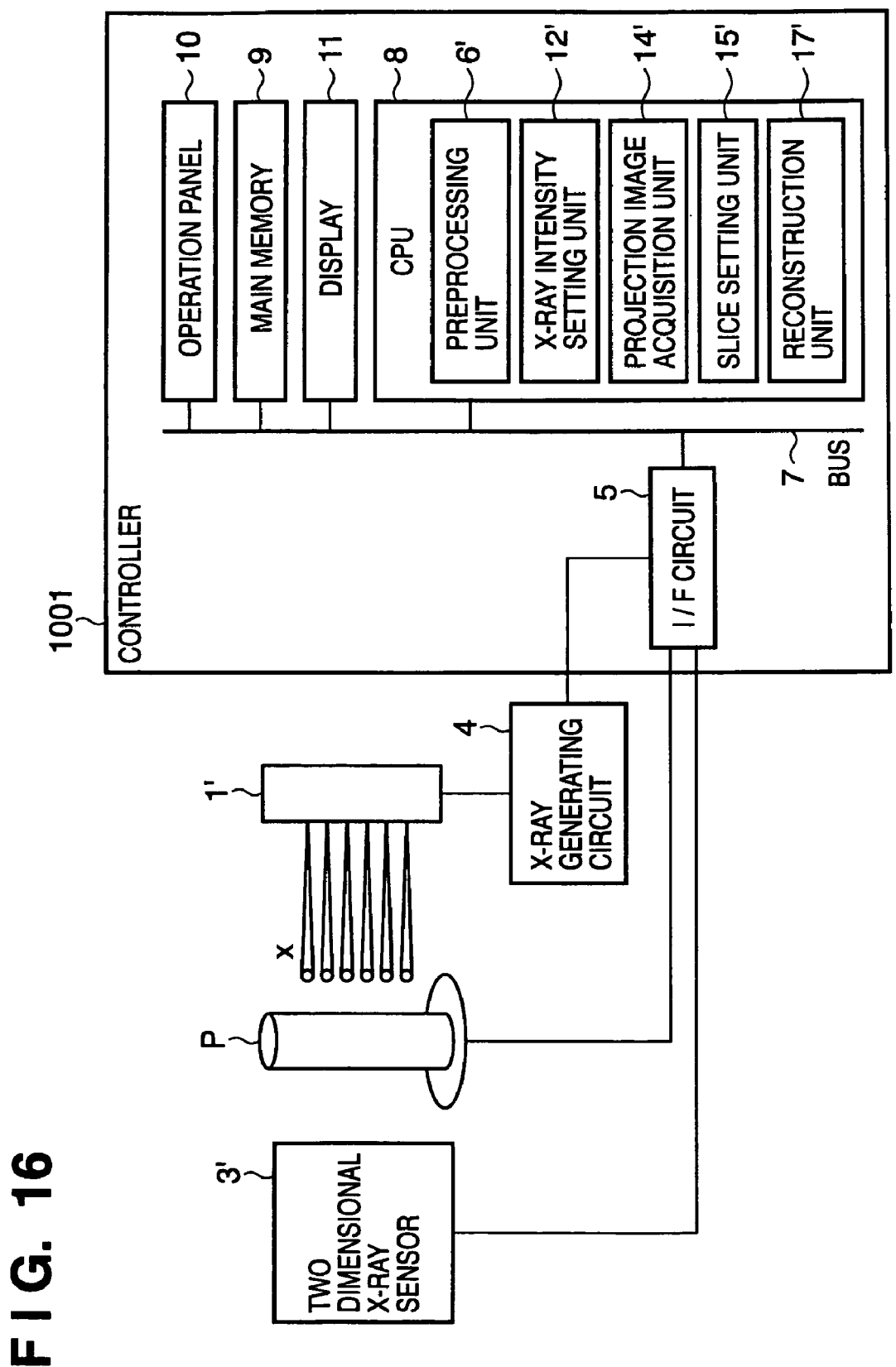
FIG. 16 is a view showing an arrangement when a radiation control apparatus is controlled using software in the system according to the second embodiment.

A radiographic imaging control apparatus shown in FIG. 16 executes the functions of the preprocessing circuit 6, X-ray intensity setting circuit 12, projection image acquisition circuit 14, slice setting circuit 15, and reconstruction circuit 17 as the functions of the CPU 8. Referring to FIG. 16, a preprocessing unit 6', X-ray intensity setting unit 12', projection image acquisition unit 14', slice setting unit 15', and reconstruction unit 17' as the functions executed by the CPU 8 correspond to the preprocessing circuit 6, X-ray intensity setting circuit 12, projection image acquisition circuit 14, slice setting circuit 15, and reconstruction circuit 17 in FIG. 1, respectively. In the radiographic imaging control apparatus shown in FIG. 16, a main memory 9 stores a program which causes the CPU 8 to execute the above-described functions.

The embodiments of the present invention have been explained in detail. The present invention can adopt embodiments in the forms of a system, apparatus, method, program, storage medium, and the like. The present invention may be applied to either a system constituted by a plurality of devices, or an apparatus consisting of a single device.

Note that the present invention includes a case wherein the functions of the embodiments are achieved by directly or remotely supplying a software program to a system or apparatus, and reading out and executing the supplied program code by a computer of that system or apparatus. The program to be supplied in this case is that corresponding to each illustrated flowcharts in the embodiments.

Therefore, the program code itself installed in a computer to implement the functional processing of the present invention using the computer implements the present invention. Put differently, the present invention includes the computer program itself for implementing the functional processing of the present invention.

In this case, the form of program is not particularly limited, and an object code, a program to be executed by an interpreter, script data to be supplied to an OS, and the like may be used as long as they have the functions of the program.

As a recording medium for supplying the program, the following media can be used. For example, a Floppy® disk, hard disk, optical disk, magneto-optical disk, MO, CD-ROM, CD-R, CD-RW, magnetic tape, nonvolatile memory card, ROM, DVD (DVD-ROM, DVD-R), and the like can be used.

As another program supply method, the user establishes a connection to a homepage on the Internet using a browser on a client computer, and downloads the computer program of the present invention from the homepage onto a recording medium such as a hard disk or the like. In this case, the program to be downloaded may be a compressed file including an automatic installation function. Also, the program code that forms the program of the present invention may be segmented into a plurality of files, which may be downloaded from different homepages. In other words, the present invention includes a WWW server which makes a plurality of users download a program file required to implement the functional processing of the present invention by the computer.

Also, a storage medium such as a CD-ROM or the like, which stores the encrypted program of the present invention, may be delivered to the user. In this case, the user who has cleared a predetermined condition may be allowed to download key information used to decrypt the encrypted program from a homepage via the Internet. The user executes the encrypted program using the downloaded key information to install the program on a computer.

The functions of the aforementioned embodiments can be implemented when the computer executes the readout program. Furthermore, the functions of the aforementioned embodiments can be implemented in collaboration with an OS or the like running on the computer based on an instruction of that program. In this case, the OS or the like executes some or all of actual processes, which implement the functions of the aforementioned embodiments.

Furthermore, some or all of the functions of the aforementioned embodiments may be implemented when the program read out from the recording medium is written in a memory equipped on a function expansion board or a function expansion unit, which is inserted in or connected to the computer. In this case, after the program is written in the function expansion board or unit, a CPU equipped on the function expansion board or function expansion unit executes some or all of actual processes based on an instruction of that program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-303538, filed on Nov. 9, 2006, which is hereby incorporated by reference herein in its entirety.

The invention claimed is:

1. A control apparatus for controlling a radiation generating apparatus having a plurality of radiation generating devices each of which generates a cone beam of radiation to irradiate a two-dimensional sensor, the control apparatus comprising:
   an input device which receives information about a part of a patient to be irradiated by the radiation generating apparatus; and
   a controller which controls the radiation generating apparatus and generates an image of the part of the patient on the basis of the information about the part of the patient,
   wherein the controller controls the radiation generating apparatus so that each of the radiation generating devices irradiates a different partial area of the two-dimensional sensor,
   wherein the controller selects two or more radiation generating devices each of which simultaneously generates one cone beam of radiation, and
   wherein the cone beams of radiation generated by the selected two or more radiation generating devices irradiate the two-dimensional sensor without overlapping each other.

2. The control apparatus according to claim 1, wherein said controller controls the radiation generating apparatus to make an intensity of the radiation with which the plurality of radiation generating devices irradiate the two-dimensional sensor correspond to the part of the patient.

3. A control apparatus for controlling a radiation generating apparatus having a plurality of radiation generating devices each of which generates a cone beam of radiation to irradiate a two-dimensional sensor, the control apparatus comprising:
   an input device which receives information about a physique of a patient to be irradiated by the radiation generating apparatus; and
   a controller which controls the radiation generating apparatus and generates an image of the physique of the patient on the basis of the information about the physique of the patient,
   wherein the controller controls the radiation generating apparatus so that each of the radiation generating devices irradiates a different partial area of the two-dimensional sensor,
   wherein the controller selects two or more radiation generating devices each of which simultaneously generates one cone beam of radiation, and
   wherein the cone beams of radiation generated by the selected two or more radiation generating devices irradiate the two-dimensional sensor without overlapping each other.

4. The control apparatus according to claim 3, wherein said controller selects the two or more radiation generating devices such that the number of radiation generating devices to be used for irradiating the two-dimensional sensor is set in accordance with the physique of the patient.

5. The control apparatus according to claim 3, wherein said controller reduces an intensity of the radiation with which the plurality of radiation generating devices irradiate the two-dimensional sensor as the physique of the patient becomes small.

6. A control apparatus for controlling a radiation generating apparatus having a plurality of radiation generating devices each of which generates a cone beam of radiation to irradiate a two-dimensional sensor, the control apparatus comprising:
   an input device which receives a radiation irradiation indication of an object to be irradiated by the radiation generating apparatus; and
   a controller which controls timing of the radiation generating apparatus and generates an image of the object on the basis of the radiation irradiation indication,
   wherein the controller controls the radiation generating apparatus so that each of the radiation generating devices irradiates a different partial area of the two-dimensional sensor in a predetermined sequence,
   wherein the controller selects two or more radiation generating devices not adjacent to each other each of which simultaneously generates one cone beam of radiation, and
   wherein the cone beams of radiation generated by the selected two or more radiation generating devices irradiate the two-dimensional sensor without overlapping each other.

7. A control method for controlling a radiation generating apparatus having a plurality of radiation generating devices each of which generates a cone beam of radiation to irradiate a two-dimensional sensor, the control method comprising the steps of:
   causing an input device to receive information about a part of a patient to be irradiated by the radiation generating apparatus; and
   causing a controller to control the radiation generating apparatus and to generate an image of the part of the patient on the basis of the information about the part of the patient,
   wherein the controller controls the radiation generating apparatus so that each of the radiation generating devices irradiates a different partial area of the two-dimensional sensor,
   wherein the controller selects two or more radiation generating devices each of which simultaneously generates one cone beam of radiation, and
   wherein the cone beams of radiation generated by the selected two or more radiation generating devices irradiate the two-dimensional sensor without overlapping each other.

8. The control method according to claim 7, wherein the controller controls the radiation generating apparatus to make an intensity of the radiation with which the plurality of radiation generating devices irradiate the two-dimensional sensor correspond to the part of the patient.

9. A control method for controlling a radiation generating apparatus having a plurality of radiation generating devices each of which generates a cone beam of radiation to irradiate a two-dimensional sensor, the control method comprising the steps of:
   causing an input device to input information about a physique of a patient to be irradiated by the radiation generating apparatus; and
   causing a controller to control the radiation generating apparatus and to generate an image of the physique of the patient on the basis of the information about the physique of the patient,
   wherein the controller controls the radiation generating apparatus so that each of the radiation generating devices irradiates a different partial area of the two-dimensional sensor, wherein the controller selects two or more radiation generating devices each of which simultaneously generates one cone beam of radiation, and wherein the cone beams of radiation generated by the selected two or more radiation generating devices irradiate the two-dimensional sensor without overlapping each other.

10. The control method according to claim 9, wherein the controller selects the two or more radiation generating devices such that the number of radiation generating devices to be used for irradiating the two-dimensional sensor is set in accordance with the physique of the patient.

11. The control method according to claim 9, wherein the controller reduces an intensity of the radiation with which the plurality of radiation generating devices irradiate the two-dimensional sensor as the physique of the patient becomes small.

12. A control method for controlling radiation generating apparatus having a plurality of radiation generating devices each of which generates a cone beam of radiation to irradiate a two-dimensional sensor, the control method comprising the steps of:

causing an input device to receive a radiation irradiation indication of an object to be irradiated by the radiation generating apparatus; and causing a controller to control timing of the radiation generating apparatus and to generate an image of the object on the basis of the radiation irradiation indication, wherein the controller controls the radiation generating apparatus so that each of the radiation generating devices irradiates a different partial area of the two-dimensional sensor in a predetermined sequence, wherein the controller selects two or more radiation generating devices not adjacent to each other each of which simultaneously generates one cone beam of radiation, and wherein the cone beams of radiation generated by the selected two or more radiation generating devices irradiate the two-dimensional sensor without overlapping each other.

13. A non-transitory computer-readable memory storing a program to execute a control method for controlling a radiation generating apparatus having a plurality of radiation generating devices each of which generates a cone beam of radiation to irradiate a two-dimensional sensor, the control method comprising the steps of:

causing an input device to receive information about a part of a patient to be irradiated by the radiation generating apparatus; and causing a controller to control the radiation generating apparatus and to generate an image of the part of the patient on the basis of the information about the part of the patient, wherein the controller controls the radiation generating apparatus so that each of the radiation generating devices irradiates a different partial area of the two-dimensional sensor, wherein the controlling selects two or more radiation generating devices each of which simultaneously generates one cone beam of radiation, and wherein the cone beams of radiation generated by the selected two or more radiation generating devices irradiate the two-dimensional sensor without overlapping each other.

14. The computer-readable memory according to claim 13, wherein the controller controls the radiation generating apparatus to make an intensity of the radiation with which the plurality of radiation generating devices irradiate the two-dimensional sensor correspond to the part of the patient.

15. A non-transitory computer-readable memory storing a program to execute a control method for controlling a radiation generating apparatus having a plurality of radiation generating devices each of which generates a cone beam of radiation to irradiate a two-dimensional sensor, the control method comprising the steps of:

causing an input device to receive information about a physique of a patient to be irradiated by the radiation generating apparatus; and causing a controller to control the radiation generating apparatus and to generate an image of the physique of the patient on the basis of the information about the physique of the patient, wherein the controller controls the radiation generating apparatus so that each of the radiation generating devices irradiates a different partial area of the two-dimensional sensor, wherein the controller selects two or more radiation generating devices each of which simultaneously generates one cone beam of radiation, and wherein the cone beams of radiation generated by the selected two or more radiation generating devices irradiate the two-dimensional sensor without overlapping each other.

16. The computer-readable memory according to claim 15, wherein the controller selects the two or more radiation generating devices such that the number of radiation generating devices to be used for irradiating the two-dimensional sensor is set in accordance with the physique of the patient.

17. The computer-readable memory according to claim 15, wherein the controller reduces an intensity of the radiation with which the plurality of radiation generating devices irradiate the two-dimensional sensor as the physique of the patient becomes small.

18. A non-transitory computer-readable memory storing a program to execute a control method for controlling a radiation generating apparatus having a plurality of radiation generating devices each of which generates a cone beam of radiation to irradiate a two-dimensional sensor, the control method comprising the steps of:

causing an input device to receive a radiation irradiation indication of an object to be irradiated by the radiation generating apparatus; and causing a controller to control timing of the radiation generating apparatus and to generate an image of the object on the basis of the radiation irradiation indication, wherein the controller controls the radiation generating apparatus so that each of the radiation generating devices irradiates a different partial area of the two-dimensional sensor in a predetermined sequence, wherein the controller selects two or more radiation generating devices not adjacent to each other each of which simultaneously generates one cone beam of radiation, and wherein the cone beams of radiation generated by the selected two or more radiation generating devices irradiate the two-dimensional sensor without overlapping each other.

* * * * *